United States Patent [19]

Pingel et al.

[11] Patent Number: 5,210,500
[45] Date of Patent: May 11, 1993

[54] PROCESS FOR CONTACTLESS MEASUREMENT OF THE ELECTRICAL RESISTANCE OF A TEST MATERIAL

[75] Inventors: Ulrich Pingel, Marl; Hans-Henning Nolte, Gelsenkirchen, both of Fed. Rep. of Germany

[73] Assignee: Flachglas Aktiengesellschaft, Gelsenkirchen, Fed. Rep. of Germany

[21] Appl. No.: 683,968

[22] Filed: Apr. 11, 1991

[30] Foreign Application Priority Data

Apr. 11, 1990 [DE] Fed. Rep. of Germany ....... 4011637
Jul. 16, 1990 [DE] Fed. Rep. of Germany ....... 4022563

[51] Int. Cl.⁵ .............................................. G01R 27/26
[52] U.S. Cl. .................................... 324/667; 324/664; 324/674; 324/693; 324/707
[58] Field of Search ................ 324/658, 663, 664, 667, 324/674, 685, 691, 693, 707, 721, 722, 724, 681, 690

[56] References Cited

U.S. PATENT DOCUMENTS

| | | | |
|---|---|---|---|
| 3,408,566 | 10/1968 | Norwich | 324/61 |
| 3,774,238 | 11/1973 | Hardway, Jr. | 324/663 |
| 3,781,672 | 12/1973 | Maltby et al. | 324/663 |
| 3,796,950 | 3/1974 | Kuecken | 324/667 X |
| 3,826,979 | 7/1974 | Steinmann | 324/61 R |
| 3,882,381 | 5/1975 | Gregory | 324/674 X |
| 3,967,191 | 6/1976 | Roche | 324/20 R |
| 3,988,669 | 10/1976 | Fasching | 324/693 X |
| 4,451,780 | 5/1984 | Ogasawara | 324/674 X |
| 4,523,142 | 6/1985 | Murata et al. | 324/693 |
| 4,554,493 | 11/1985 | Armstrong | 318/444 |
| 4,924,172 | 5/1990 | Holmagren | 324/664 |
| 4,968,947 | 11/1990 | Thorn | 324/701 |

FOREIGN PATENT DOCUMENTS

| | | |
|---|---|---|
| 0192416 | 8/1986 | European Pat. Off. |
| 0324193 | 7/1989 | European Pat. Off. |
| 1083978 | 6/1960 | Fed. Rep. of Germany |
| 2115437 | 10/1972 | Fed. Rep. of Germany |
| 2659073 | 7/1977 | Fed. Rep. of Germany |
| 2857389 | 5/1980 | Fed. Rep. of Germany |
| 2952825 | 9/1980 | Fed. Rep. of Germany |
| 3120522 | 12/1982 | Fed. Rep. of Germany |
| 3528009 | 2/1987 | Fed. Rep. of Germany |
| 3314770 | 11/1987 | Fed. Rep. of Germany |
| 3717050 | 12/1988 | Fed. Rep. of Germany |
| 3804218 | 8/1989 | Fed. Rep. of Germany |

Primary Examiner—Jack B. Harvey
Assistant Examiner—Glenn W. Brown
Attorney, Agent, or Firm—Sixbey, Friedman, Leedom & Ferguson

[57] ABSTRACT

Process for contactless measurement of the electrical resistance (or of the electrical conductivity) of a preferably flat material (test material) in which an alternating current is capacitively coupled into the test material with the help of two coupling electrodes. The total impedance is measured at at least three different frequencies, and from that measurement, the stray capacitance between the two coupling electrodes, the coupling capacitance between the two coupling electrodes and the test material, as well as the resistance of the test material are determined. In a preferred embodiment the process is used for controlling the windshield wipers of a motor vehicle.

18 Claims, 8 Drawing Sheets

PROCESS FOR CONTACTLESS MEASUREMENT OF THE ELECTRICAL RESISTANCE OF A TEST MATERIAL

BACKGROUND OF THE INVENTION

The invention relates to a process for contactless measurement of the electrical resistance (or of the electrical conductivity) of a preferably flat material (test material), in which an alternating current is capacitively put into the test material with the help of two coupling electrodes.

DESCRIPTION OF RELATED ART

Processes of the above-mentioned type are known in many cases (see, German Offenlegunsschrifts 2 239 359 and 38 15 011, published European Applications 0 192 416 and 0 324 193, and U.S. Pat. Nos. 3,408,566, 3,967,191 and 4,554,493). All known processes of the type being discussed have in coma on that the measurement of the electrical resistance (or of the electrical conductivity) is not sufficiently precise.

SUMMARY OF THE INVENTION

Consequently, the object of the invention is to configure and further develop the process described basically above so that the electrical resistance (or the electrical conductivity) of a test material can be measured relatively simply with improved precision; in particular, measuring errors that occur in the prior art, for example, due to changes in the distance between the test material and the coupling electrodes, are to be reduced.

The process according to the invention, in which the above-indicated object is achieved, is characterized, first of all, essentially in that a total impedance is measured at at least three different frequencies and from the measurements, the stray capacitance between the two coupling electrodes, the coupling capacitance between the two coupling electrodes and the test material, and the resistance of the test material are determined.

The invention is based on the known fact that when two electrically conductive surfaces (called coupling electrodes, here) are brought near a conductive medium (called a test material here), a capacitance (called a coupling capacitance, here) develop: between the coupling electrodes and the test material. The invention is further based on the fact, previously not taken into account from a measurement standpoint, that a capacitance (called a stray capacitance, here) also develops between the two coupling electrodes. Therefore, a total impedance consisting of the stray capacitance, the coupling capacitance and the resistance to be measured is active for the alternating current that is flowing because of an alternating voltage applied to the coupling electrodes. Here, the stray capacitance is parallel to the series connection of the coupling capacitance and the resistance to be measured.

A preferred embodiment of the process according to the invention that is of special importance is characterized in that the total impedance is measured with a high-frequency alternating current and, from that, the stray capacitance between the two coupling electrodes is determined. Also, the total impedance is measured with a low-frequency alternating current and, from that measurement, taking the stray capacitance into account, the coupling capacitance between the two coupling electrodes and the test material is determined. Furthermore, the total impedance is measured with an alternating current of a frequency between the high and the low frequency and, from that measurement, taking the stray capacitance and the coupling capacitance into account, the resistance of the test material is determined. Here, the invention exploits the fact that the coupling electrodes can be dimensioned, and the distances can be arranged, so that the stray capacitance is small compared to the coupling capacitance. Then, at relatively high frequency, the total impedance is determined essentially by the low ohmic stray capacitance at high frequency; the phase shift is almost 90° between the applied alternating voltage and the flowing alternating current, at relatively low frequency, the total impedance is determined essentially by the high ohmic coupling capacitance at low frequency; in this case also, the phase shift is almost 90° between the applied alternating voltage and the flowing alternating current.

Between the high frequency and the low frequency there exists a frequency at which the phase shift between the applied alternating voltage and the flowing alternating current is at a minimum. Therefore, the real part of the total impedance, preferably, is measured with an alternating current of the frequency at which a phase shift minimum occurs.

From the three measurements to be made according to the invention, i.e., measurement of the total impedance with a high-frequency alternating current, measurement of the total impedance with a low-frequency alternating current and measurement of the total impedance with an alternating current of a frequency between the high and the low frequency, the stray capacitance, the coupling capacitance and the resistance to be measured can then be determined.

If the process according to the invention is performed, e.g., with stationary-mounted coupling electrodes, then the stray capacitance and/or the coupling capacitance can be obtained from a single measurement, so that, then, to determine the resistance of the test material, only routine measurements at two frequencies or at one frequency are necessary.

Specifically, now, there are various possibilities for configuring and further developing the process according to the invention which, along further objects, features and advantages of the present invention, will become apparent from the following description when taken in connection with the accompanying drawings which show, for purposes of illustration only, a preferred embodiment in accordance with the present invention.

DETAILED DESCRIPTION OF THE PREFERRED EMBODIMENT

Figure 1:
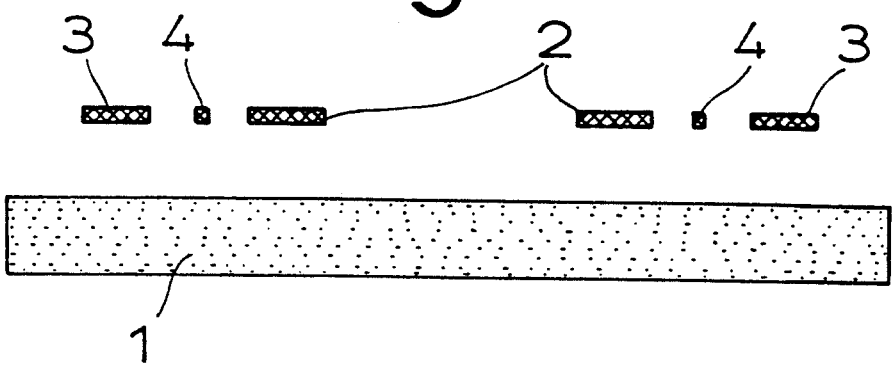
FIG. 1 is a cross section through a preferred embodiment of an arrangement for performing the process according to the invention.
Figure 2:
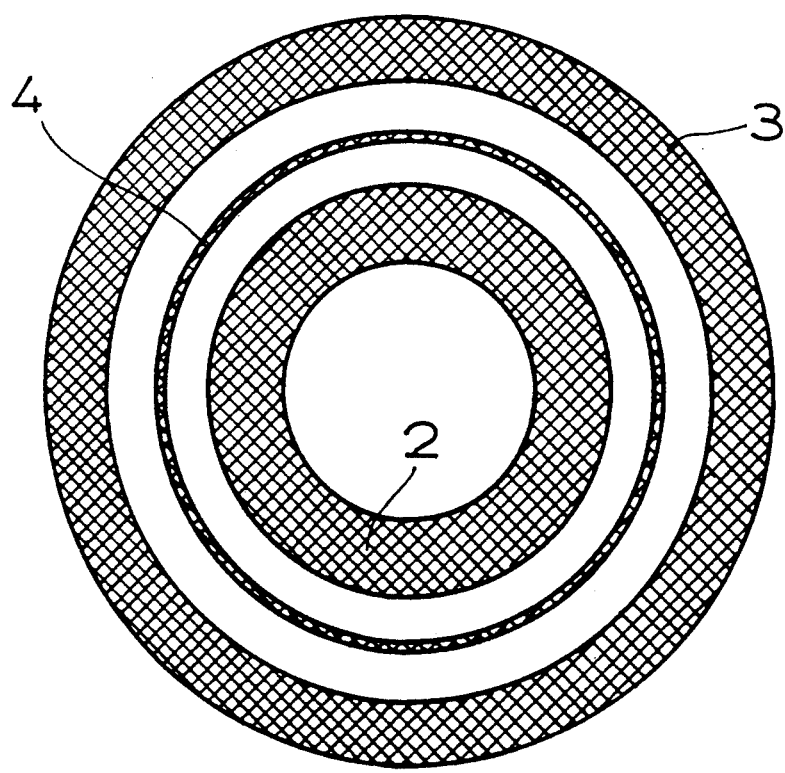
FIG. 2 is a top view of the arrangement according to FIG. 1.

FIGS. 1 and 2 show the mechanical design of a preferred embodiment of an arrangement for performing the process according to the invention, i.e., a process for contactless measurement of the electrical resistance (or of the electrical conductivity) of a test material 1, and by which an alternating current is capacitively put into a test material 1 with the help of two coupling electrodes 2, 3. FIGS. 1 and 2 show, in this respect, a preferred embodiment of an arrangement for performing the process according to the invention in which coupling electrodes 2, 3 are made equal in cross-sectional area and another decoupling electrode 4 is provided in addition to two coupling electrodes 2, 3, concentrically between them.

Figure 3:
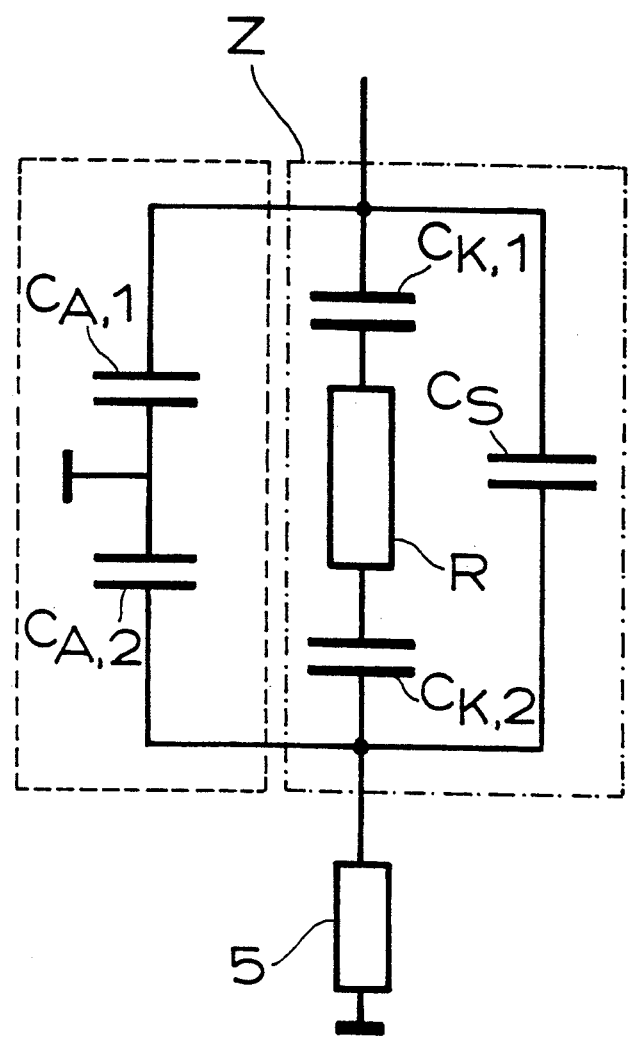
FIG. 3 is the equivalent circuit diagram for the arrangement according to FIGS. 1 and 2, supplemented with a measuring resistance.

FIG. 3 now shows the equivalent circuit diagram on which the process according to the invention is based. First of all, resistance R is the electrical resistance of the test material 1 that is to be contactlessly measured with the help of the process according to the invention. Further, the two element coupling capacitances $C_{K,1}$ and $C_{K,2}$ of the circuit represented in FIG. 3 are the capacitances between coupling electrode 2 and test material 1 and between coupling electrode 3 and test material 1. Together, the element coupling capacitances $C_{K,1}$ and $C_{K,2}$ form a coupling capacitance $C_K$. Further, a stray capacitance $C_S$ of the circuit represented in FIG. 3 is the capacitance between the two coupling electrodes 2 and 3.

It has already been explained above that, in the embodiment represented, another decoupling electrode 4 is provided between two coupling electrodes 2 and 3. Decoupling electrode 4 acts to reduce the influence of stray capacitance $C_S$ and is placed at ground potential; current flowing by stray capacitance $C_S$ is decoupled. In the electric circuit shown in FIG. 3, the two element decoupling capacitances $C_{A,1}$ and $C_{A,2}$ represent the decoupling electrode 4.

In the circuit represented in FIG. 3, resistor R, two element coupling capacitances $C_{K,1}$ and $C_{K,2}$ or coupling capacitance $C_K$ and stray capacitance $C_S$ form total impedance Z. A measuring resistance 5 is additionally provided.

Figure 4:
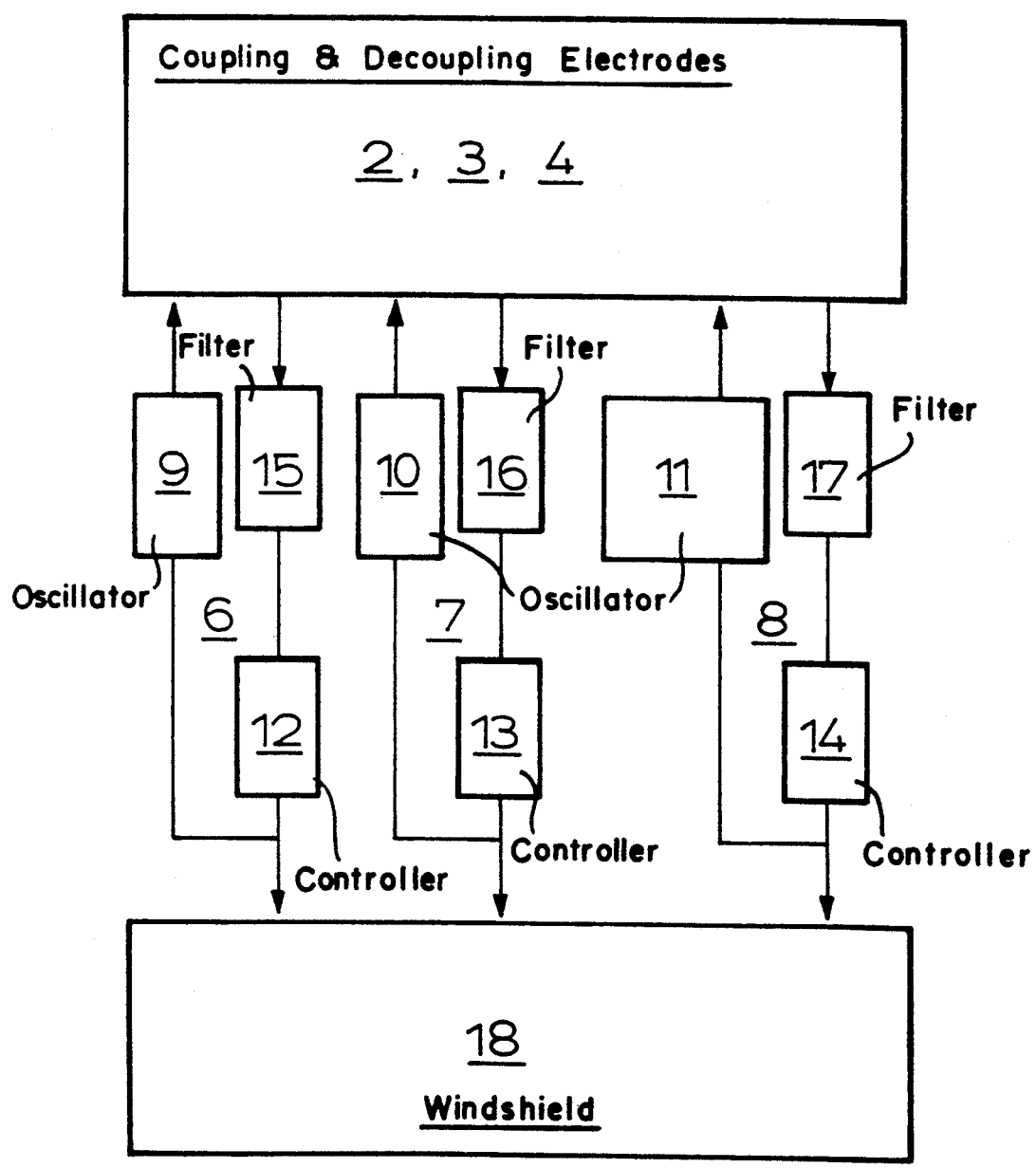
FIG. 4 is a block diagram of a possible evaluation circuit for use in the process according to the invention.

FIG. 4 shows a block diagram of a possible evaluation circuit for use in the process according to the invention. In the upper part of the block diagram represented in FIG. 4, the two coupling electrodes 2 and 3 and the decoupling electrode 4 are combined. Further, the evaluation circuit contains a supply part 6 for a high-frequency alternating voltage, a supply part 7 for a low-frequency alternating voltage and a supply part 8 for an alternating voltage with a changeable frequency lying between the high and low frequencies. An oscillator 9, 10, 11, a controller 12, 13, 14 and a filter 15, 16, 17 are part of each supply part 6, 7, 8. Finally, a computer 18 is provided that performs the evaluations, individually, specifically with the help of the following equations:

$$Z = \frac{\omega^2 R C_K^2 - j\omega(C_S + C_K + \omega^2 R^2 C_S C_K^2)}{(\omega^2 R C_S C_K)^2 + \omega^2(C_S + C_K)^2} \quad (1)$$

$$X_I = -\frac{C_S + C_K + \omega^2 R^2 C_S C_K^2}{\omega^3 R^2 C_S^2 C_K^2 + \omega(C_S + C_K)^2} \quad (2)$$

$$X_R = \frac{R C_K^2}{(\omega R C_S K_R)^2 + (C_S + C_K)^2} \quad (3)$$

$$C_S \sim -(\omega_1 X_I)^{-1} \quad (4)$$

$$C_K \sim -\frac{1}{\omega_3 X_I} - C_S \quad (5)$$

$$R \sim \frac{1}{2\omega_2^2 X_R C_S} \left( 1 - \sqrt{1 - \left( \frac{2\omega_2 X_R C_S (C_S + C_K)}{C_K} \right)^2} \right) \quad (6)$$

with
Z = total impedance,
$X_I$ = imaginary part of the total impedance,
$X_R$ = real part of the total impedance,
$C_S$ = stray capacitance,
$C_K$ = coupling capacitance,
R = resistance.

Here, equations (1), (2) and (3) result from the exact conversion of the equivalent circuit diagram that is the basis of the process according to the invention. Equations (4), (5) and (6) are based on approximations with frequencies $\omega_1 > \omega_2 > \omega_3$, and $\omega_2$ is in the range of the phase shift minimum.

According to the invention, the process proceeds such that, in a first step, imaginary part $X_I$ of total impedance Z is measured with a high-frequency alternating current and, from that measurement, stray capacitance $C_S$ between the two coupling electrodes 2 and 3 is determined, specifically, with the help of equation (4). Then, in a second step, imaginary part $X_I$ of the total impedance is measured with a low-frequency alternating current and, from that, taking stray capacitance $C_S$ into account, coupling capacitance $C_K$ between two coupling electrodes 2 or 3 and test material 1 is determined, specifically, with the help of equation (5). Finally, in a third step, real part $X_R$ of the total impedance is measured with an alternating current of a frequency lying between the high and the low frequencies, namely with an alternating current of the frequency at which a phase shift minimum occurs and from that, taking stray capacitance $C_S$ and coupling capacitance $C_K$ into account, resistance R of test material 1 is determined, specifically, with the help of equation (6).

It is not represented in the figures that, to further increase the measurement precision, the measurements can be performed with two identical electrode arrangements at a defined, varying distance to test material 1.

Depending on the configuration of the coupling electrodes and/or on the distance between the coupling electrodes and the test material, a contraction of the electric field lines can occur, which results in a change in the effective area of the coupling electrodes and thus, in an additional change in the measured resistance. A calibration of this effect, making a calibration curve for resistance R as a function of the ratio of stray capacitance $C_S$ to coupling capacitance $C_K$, as well as an effective correction, can be achieved by evaluating the measured values of the stray capacitance and of the coupling capacitance.

Further, the dependence of the capacitance values on the spacing of the coupling electrodes can be set for the purpose of spacing control, and a contactless measurement at a small distance (high measurement precision) is possible without danger of collision. Another advantage is the elimination of the otherwise necessary spacing sensors.

It has been explained above that, in the equivalent circuit diagram represented in FIG. 3, another measuring resistance 5 is provided. The alternating voltage is applied to measuring resistance 5 at the series connection from the electrode arrangement. The voltage drop at measuring resistance 5 is used as a measurement of the flowing alternating current. Here, measuring resistance 5 is dimensioned so that the voltage drop at measuring resistance 5 is small as compared to the total alternating voltage applied.

Figure 5:
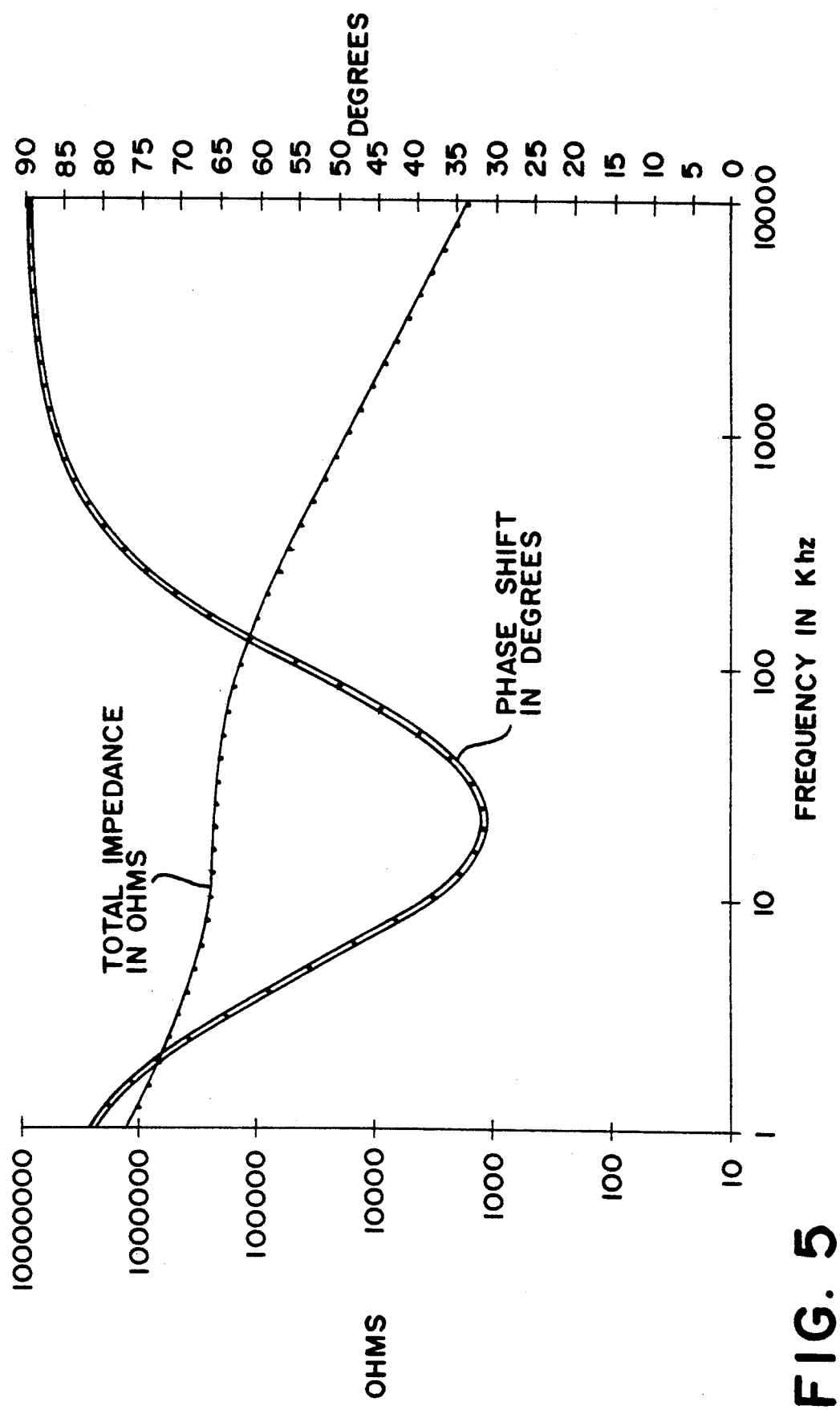
FIG. 5 is a graphic representation of the amount of the total impedance and of the phase shift as a function of the frequency.
Figure 6:
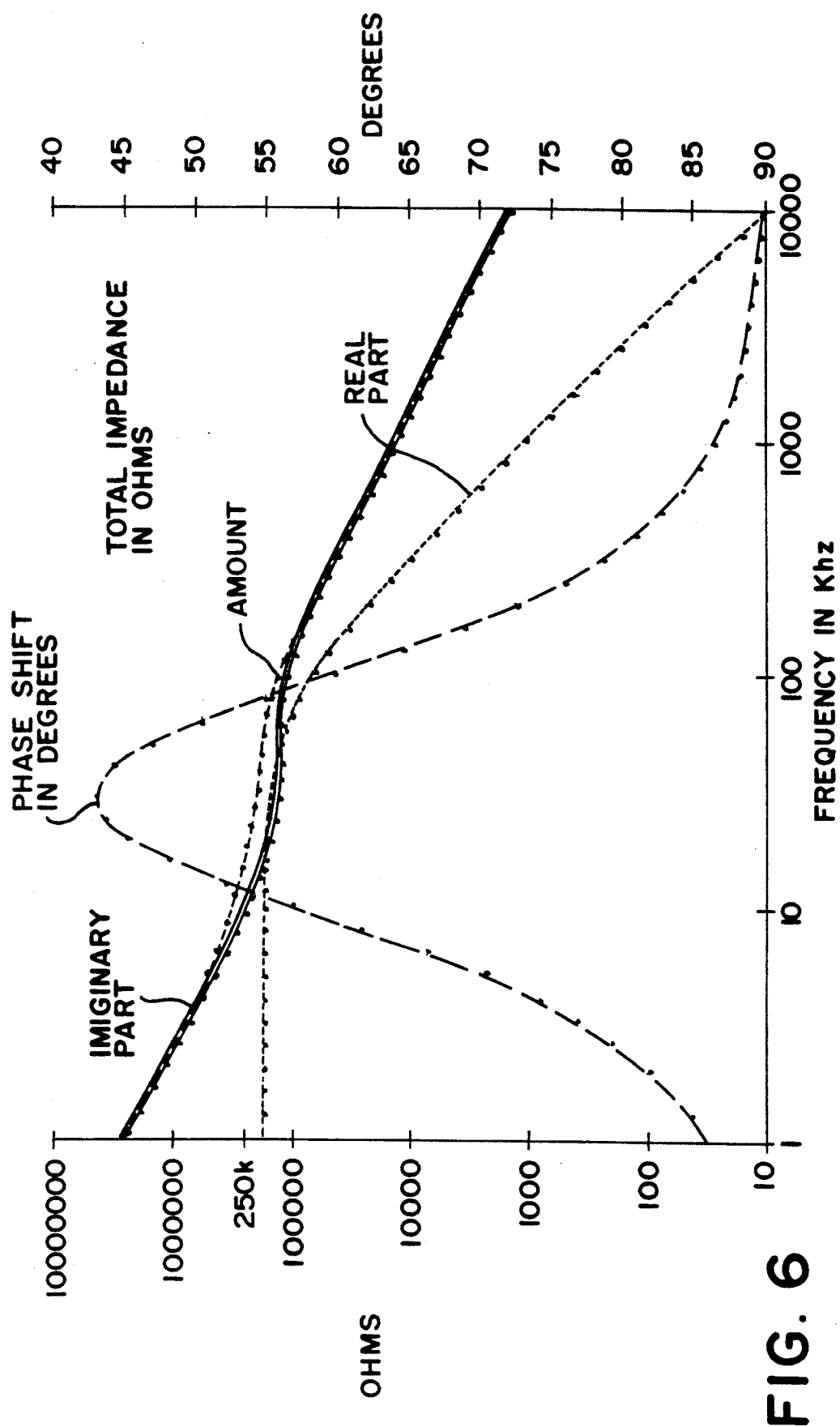
FIG. 6 is a graphic representation of the amount of the total impedance, of the imaginary part of the total impedance, of the real part of the total impedance, and of the phase shift as a function of the frequency.

FIGS. 5 and 6 very clearly show that, when the applied alternating voltage has a relatively high frequency, the phase shift between the applied alternating voltage and the flowing alternating current is almost 90° and that, when the applied alternating voltage has a relatively low frequency, the phase shift between the applied alternating voltage and the flowing alternating current is also almost 90°. FIGS. 5 and 6 also show very clearly that, between the high frequency and the low frequency, there exists a frequency at which the phase shift between the applied alternating voltage and the flowing current is at a minimum.

Figure 7:
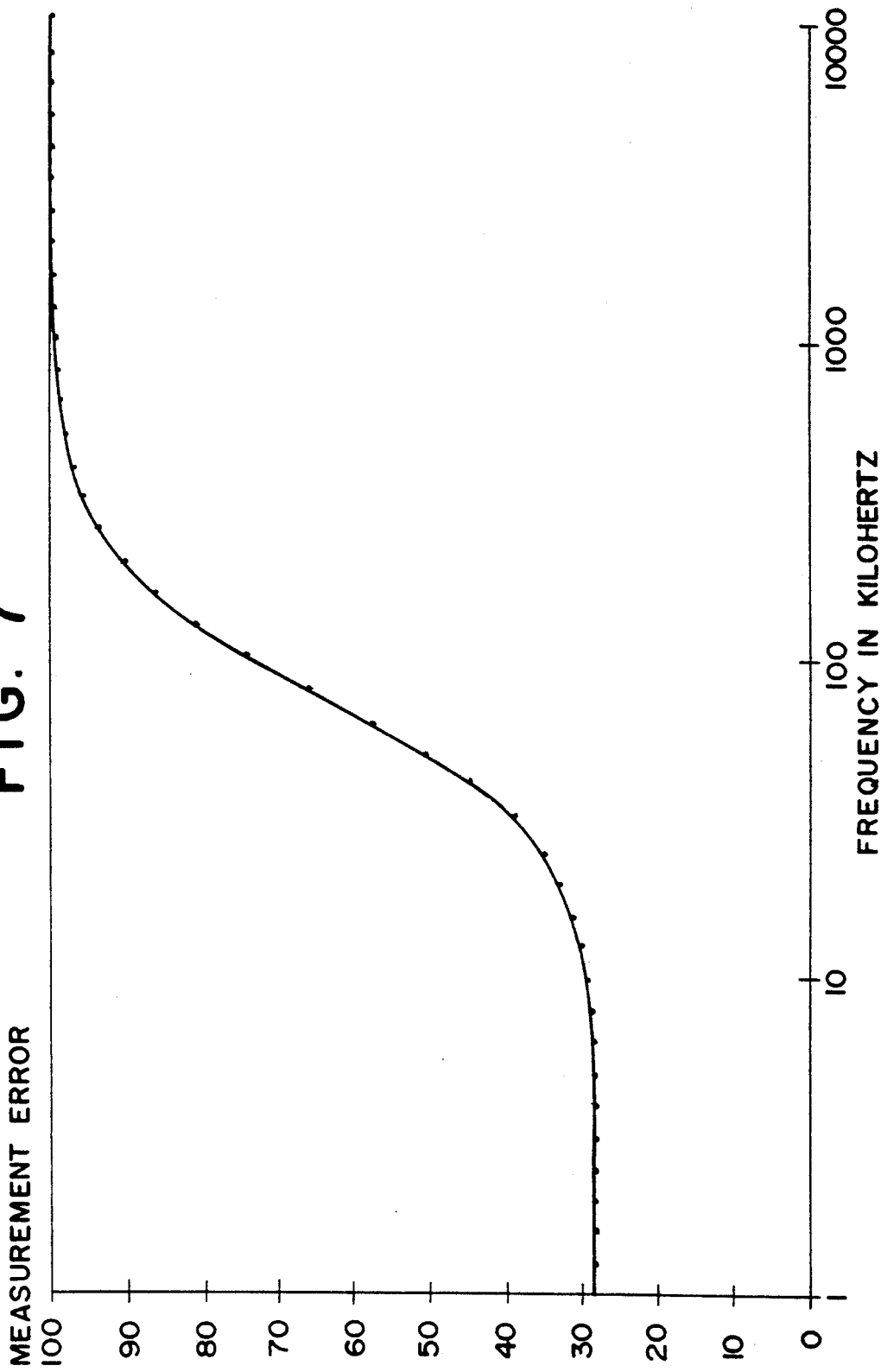
FIG. 7 is a graphic representation of the measurement error occurring, not taking the stray capacitance into account.

It can be seen from FIG. 7 that, when stray capacitance $C_S$ is not taken into account, a considerable measurement error occurs. At a low frequency, this measurement error is almost 30% and, at the frequency at which a phase shift minimum occurs, it is almost 40%; above the frequency at which a phase shift minimum occurs, the relative measurement error increases very rapidly to 100%.

Further, FIGS. 5 to 7 show the conditions for the case in which stray capacitance $C_S$ is 10 pF, coupling capacitance $C_K$ is 66 pF and resistance R is 260 kilohms.

The process according to the invention can be used for contactless measurement of the electrical resistance (or of the electrical conductivity) of the most varied materials, e.g., for contactless measurement of the electrical resistance (or of the electrical conductivity) of plastic sheets, paper strips, etc.; it is suited for determining resistances in the range of about 10 to $10^6$ ohms/cm$^2$.

Figure 8:
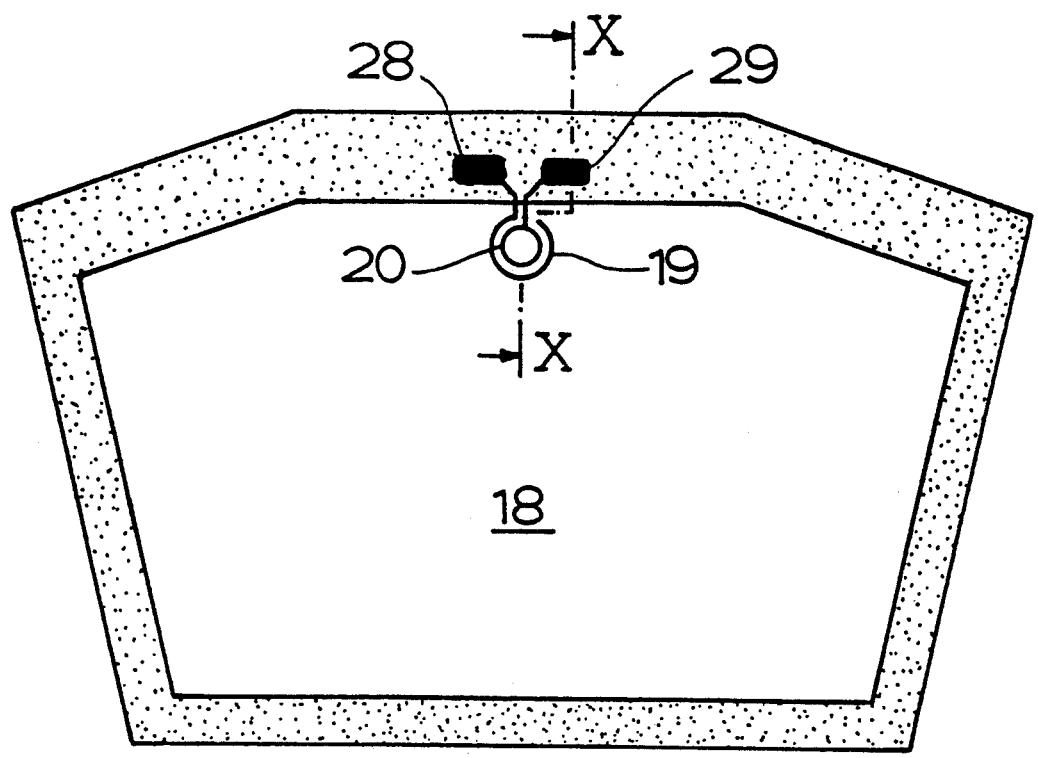
FIG. 8 diagrammatically depicts a windshield of a motor vehicle with a control device based on the process according to the invention to control the windshield wiper or wipers.
Figure 9:
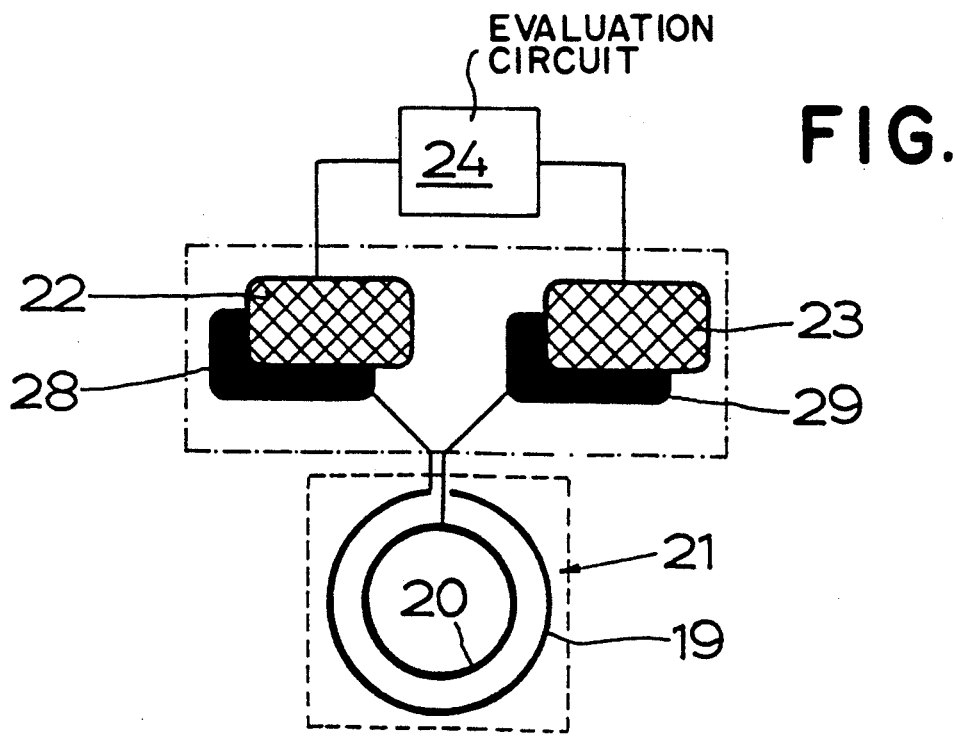
FIG. 9 is a partial perspective view of the control device according to FIG. 8, enlarged relative thereto.
Figure 10:
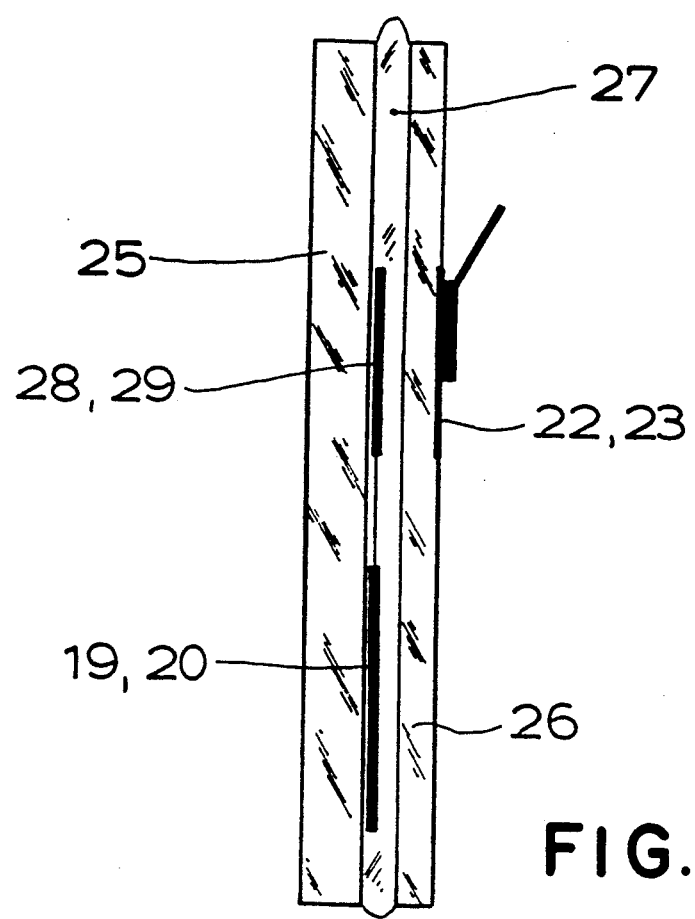
FIG. 10 is a section taken along line X—X in FIG. 8, enlarged relative thereto.

The process according to the invention can be used, especially well, to control the windshield wiper or wipers of windshield 18 of a motor vehicle indicated in FIGS. 8 and 10. Consequently, the object of the invention is also a control device for controlling the windshield wiper or wipers of windshield 18 of a motor vehicle. A sensor 21, comprising of at least two coupling electrodes 19, 20, at least two contact elements 22, 23 and an evaluation circuit 24 connected to contact elements 22, 23 belong to such a control device, as FIGS. 8 to 11, taken together, show.

Basically, the coupling electrodes could be DC-connected to the contact elements 22, 23. Generally, windshield 18 of a motor vehicle is made as a laminated pane with an outer glass pane 25, an inner glass pane 26 and a safety sheet 27 provided between outer glass pane 25 and inner glass pane 26. Then, it is advisable that the embodiment, of a control device for controlling the windshield wiper or wipers of windshield 18 of a motor vehicle that is represented in FIGS. 8 to 11, have the coupling electrodes 19, 20 contact electrodes 28, 29 provided between outer glass pane 25 and safety sheet 27, with the coupling electrodes 19, 20 being DC-connected to contact electrodes 28, 29. Contact elements 22, 23 for contact electrodes 28, 29, are provided on the side of inner glass pane 26 that is facing away from safety sheet 27. Thus, a capacitive coupling is achieved between the contact electrodes 28, 29 and contact elements 22, 23. Instead of such a capacitive coupling, an inductive coupling could also be achieved. Basically, when the windshield is made as a laminated pane, there exists the possibility of DC-connecting the coupling electrodes to the contact elements.

The control device according to the invention for controlling the windshield wiper or wipers of the windshield of a motor vehicle is based on the detection of the complex total impedance between two or more coupling electrodes at at least three different frequencies. The capacitively coupled alternating current is influenced by water on the windshield. On the one hand, the dielectric properties of water increase the measurable capacitance between the coupling electrodes. On the other hand, an additional capacitance develops between a water film and the coupling electrodes, a capacitance that results in an alternating current through the water film. When determining the complex total impedance, the capacitive imaginary part of the complex total impedance and the real part of the complex total impedance are detected as has already been described above.

To classify water on the windshield of a motor vehicle, the water can be thought of in a simplified way by a combination of extreme cases, namely
a) thick water film distributed evenly,
b) thin water film distributed evenly,
c) large, individual, dot-shaped water drops,
d) small, individual, dot-shaped water drops.

In such cases, the following relationship is observed between the capacitive imaginary part of the complex total impedance and the real part of the complex total impedance as a function of the water on the windshield:

a) An evenly distributed water film generates a low ohmic resistance that is an approximately hyperbolic function of the thickness of the water film. In contrast, dot-shaped water drops represent a high ohmic resistance.

b) The stray capacitance of the coupling electrodes changes mainly according to the amount of water in the electric field and essentially is not a function of the water being in the form of a water film or in the form of individual, dot-shaped water drops.

c) When the water is present as a water film, only a coupling capacitance is active between the coupling electrodes and the water.

To control the windshield wiper, it is now desirable to obtain, in addition to a measurement value for the amount of water, also information about the distribution of the water—water film or water drops. For this purpose, the values of the stray capacitance, the coupling capacitance and the resistance are determined by three measurements with differing frequencies. Then, using the capacitance values and the resistance values, as well as their change over time, information can be derived about the water on the windshield, i.e., the amount of water and whether the water is in the form of a film or dot-shaped water drops. The information obtained is, then, used to control the windshield wiper.

Figure 11:
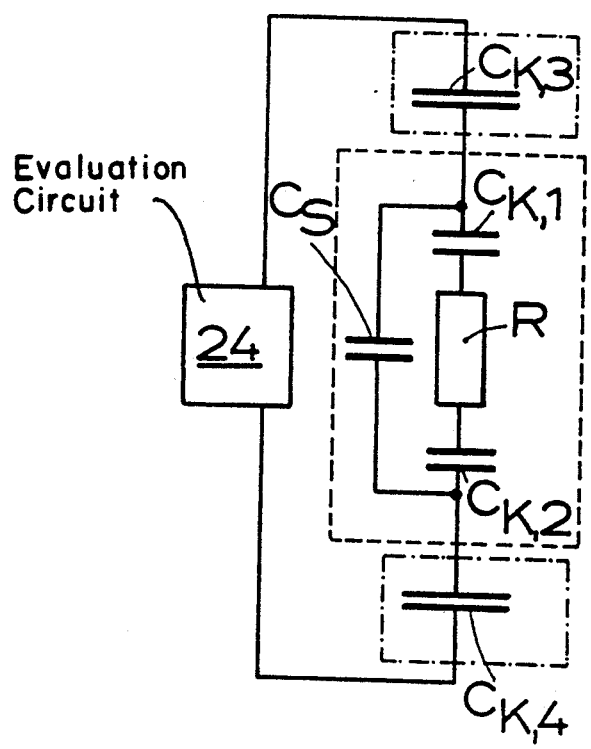
FIG. 11 is an equivalent circuit diagram for the control device according to FIGS. 8 to 10.

The equivalent circuit diagram represented in FIG. 11 for the control device according to FIGS. 8 to 10 corresponds essentially to the equivalent circuit diagram represented in FIG. 3 for the arrangement according to FIGS. 1 and 2. Additionally, element coupling capacitances $C_{K,3}$ and $C_{K,4}$ between contact elements 22, 23 and contact electrodes 28, 29 are drawn in here.

When using the process according to the invention for controlling the windshield wiper or wipers of the windshield of a motor vehicle, preferably the total impedance is measured at five different frequencies, preferably between 200 Hz and 5 MHz.

Since, when using the process according to the invention for controlling the windshield wiper or wipers of the windshield of a motor vehicle, sensor 21 is not always wetted evenly with water, the curves represented in FIGS. 5 to 7 are blurred. Therefore, the measurement values are evaluated so that, on the one hand, the imaginary part of the total impedance and the real part of the total impedance are calculated at all measurement points, and on the other hand, the determined values or the determined curves are compared with known values or with known curves.

Further, it is advisable to differentiate between four types of wetting, namely,
a) dry,
b) slightly sprayed
c) drops,
d) continuous water film.

Here, the following is determined:
a) Dry: constant and low capacitance values, no ohmic impedances in the entire frequency range.
b) Slightly sprayed: High capacitance in the lower frequency range, low capacitance in the high frequency range, high ohmic impedances in the medium frequency range, low ohmic impedances in the high frequency range.
c) Drops: Medium capacitance at low and medium frequencies. Rise in ohmic impedances in the high frequency range.
d) Continuous water film: High capacitance at low and medium frequencies. Rise in ohmic impedances in the high frequency range.

On this basis, evaluation circuit 24 can compare the measured values with these combinations of values to assess whether and to what degree (intermittent, slow, fast, etc.) the wipers should be activated.

Of course numerous other applications for the inventive process will now have become clear to those skilled in the art as will other means for implementing it. Thus, the present invention should not be viewed as being limited to the preferred embodiment described herein. Instead, the invention should be considered as encompassing the full scope of the appended claims.

We claim:

1. Process for contactless measurement of at least one of the electrical resistance and the electrical conductivity of a test material comprising the steps of applying an alternating voltage to the test material by two coupling electrodes and thus, capacitively coupling an alternating current into the test material at at least three different frequencies via the two coupling electrodes, measuring a total impedance that corresponds to a coupling capacitance between the coupling electrodes and the test material, a stray capacitance between the coupling electrodes, and the resistance of the test material, and from the total impedance measured, determining the stray capacitance between the two coupling electrodes, the coupling capacitance between the two coupling electrodes and the test material, as well as the resistance of the test material.

2. Process according to claim 1, wherein the steps of capacitively coupling an alternating current into the test material at at least three different frequencies and measuring the total impedance comprise: measuring a first value of total impedance with a high-frequency alternating current and from the first value of total impedance measured, determining the stray capacitance between the two coupling electrodes; measuring a second value of total impedance with a low-frequency alternating current and from the second value of total impedance measured, taking the stray capacitance between the two coupling electrodes into account, determining the coupling capacitance between the two coupling electrodes; and measuring a third value of total impedance with an alternating current of a frequency between the high and the low frequency alternating currents, and from the third value of total impedance measured, taking the stray capacitance between the two coupling electrodes and the coupling capacitance between the two coupling electrodes and the test material into account, determining the resistance of the test material.

3. Process according to claim 2, wherein a real part of the total impedance is measured with an alternating current having a frequency at which a phase shift minimum occurs between the alternating voltage applied to by the coupling electrodes and the coupled alternating current.

4. Process according to claim 1, in which the coupling electrodes are stationary; wherein at least one of the stray capacitance and the coupling capacitance is determined only once.

5. Process according to claim 1, wherein the capacitive coupling of the alternating current into the test material is performed with coupling electrodes that are equal in cross-sectional area.

6. Process according to claim 5, wherein the capacitive coupling of the alternating current into the test material is performed with coupling electrodes made as concentric rings.

7. Process according to claim 6, wherein, to reduce the influence of the stray capacitance, a part of the current flowing by the stray capacitance is decoupled by a decoupling electrode lying between the coupling electrodes.

8. Process according to claim 7, wherein, to increase the measurement precision, the total impedance is measured with two identical arrangements of said coupling electrodes, said arrangements being located at a two different defined distances from the test material.

9. Process according to claim 1, wherein the measuring of the impedance is performed with an electrode arrangement having several concentric rings and each of the concentric rings is operated alternatively as coupling electrode, as a ground electrode and without a specific potential.

10. Process according to claims 1, wherein the measuring of impedance is performed with an electrode arrangement into which a temperature measurement device is integrated and used to compensate for the influence of temperature.

11. Process according to claim 1, wherein the measured values of at least one of the stray capacitance and the coupling capacitance is used to control the spacing between the electrode arrangement and the test material.

12. Process according to claim 1, wherein the stray capacitance, the coupling capacitance and the resistance determined are used for controlling a windshield wiper of a motor vehicle.

13. Process according to claim 12, wherein the total impedance is measured at at least five different frequencies.

14. Process according to claim 13, wherein said at least 5 frequencies are between 200 Hz and 5 MHz.

15. Process according to claim 1, wherein the capacitive coupling of the alternating current into the test material is performed with coupling electrodes made as concentric rings.

16. Process according to claim 1, wherein, to reduce the influence of the stray capacitance, a part of the current flowing by the stray capacitance is decoupled by a decoupling electrode lying between the coupling electrodes.

17. Control device for controlling a windshield wiper of a motor vehicle, comprising a sensor consisting of at least two coupling electrodes, at least two contact elements coupled to the coupling electrodes, means for applying an alternating voltage to a windshield by the two coupling electrodes and thus, capacitively coupling an alternating current into the windshield at at least three different frequencies via the two coupling electrodes, an evaluation circuit connected to contact elements as means for detecting a complex total impedance, that corresponds to a coupling capacitance between the coupling electrodes, a stray capacitance between the coupling electrodes, and the resistance of the windshield and any water thereon, acting between the coupling electrodes at said at least three different frequencies as a function of a water-influenced, capacitively coupled alternating current and a capacitance, which is affected by the dielectric properties of water, measured between the coupling electrodes; wherein said means for detecting comprises means for measuring said total complex impedance and for determining the stray capacitance between the two coupling electrodes, the coupling capacitance between the two coupling electrodes and the windshield as well as the resistance of the windshield and any quantities of water thereon from the total complex impedance measured, and means for controlling operation of the windshield wiper as a function of the amount of any quantities of water on the windshield and the manner in which said water is distributed thereon.

18. Control device according to claim 17, wherein the coupling electrodes and the contact elements are incorporated into a windshield made of a laminated glass having an outer glass pane, an inner glass pane and a safety sheet provided between the outer glass pane and the inner glass pane, the coupling electrodes and two contact electrodes being provided between the outer glass pane and the safety sheet; wherein the coupling electrodes are conductively coupled to the contact electrodes, and each of the contact elements is associated with a respective one of the contact electrodes and is provided on a side of the inner glass pane facing away from the safety sheet.

* * * * *